US006361957B1

(12) United States Patent
Javitt

(10) Patent No.: US 6,361,957 B1
(45) Date of Patent: Mar. 26, 2002

(54) ASSAY FOR D-SERINE TRANSPORT ANTAGONIST AND USE FOR TREATING PSYCHOSIS

(75) Inventor: Daniel C. Javitt, Riverdale, NY (US)

(73) Assignee: Glytech, Inc.

( * ) Notice: Subject to any disclaimer, the term of this patent is extended or adjusted under 35 U.S.C. 154(b) by 0 days.

(21) Appl. No.: 09/365,889

(22) Filed: Aug. 3, 1999

(51) Int. Cl.$^7$ ...................... G01N 33/53; G01N 33/566; A01N 37/44

(52) U.S. Cl. .................. 435/7.1; 435/7.2; 436/501; 436/503; 436/504; 514/561

(58) Field of Search ........................... 514/42, 45, 561, 514/551, 578, 49, 458, 474, 554, 663, 762, 563; 436/501, 503, 504; 435/4, 7.1, 7.2

(56) References Cited

U.S. PATENT DOCUMENTS

| | | |
|---|---|---|
| 4,904,681 A | 2/1990 | Cordi et al. |
| 5,068,412 A | 11/1991 | Ohfune et al. |
| 5,086,072 A | 2/1992 | Trullas et al. |
| 5,179,085 A | 1/1993 | Bigge et al. |
| 5,187,171 A | 2/1993 | Cordi et al. |
| 5,260,324 A | 11/1993 | Cordi et al. |
| 5,428,069 A | 6/1995 | Skolnick et al. |

FOREIGN PATENT DOCUMENTS

WO WO/97/20553 A1 6/1997

OTHER PUBLICATIONS

Sershen et al., J. of Neurochemistry, vol. 32, p. 719–726, 1979.*
A. Hashimoto, et al. "Extracellular Concentration of Endogenous Free D–Serine in the Rat Brain as Revealed by in Vivo Microdialysis"Neuroscience vol. 66 No. 3, pp. 635–643, 1993.
Henry Sershen, et al. "Inhibition Pattern By Analogs Indicates the Presence of Ten or More Transport Systems for Amino Acids in Brain Cells" Journal of Neurochemistry, vol. 32, pp. 719–726, 1978.
Edmund A. Debler, et al. "High–Affinity Transport of γ–Aminobutyric Acid, Glycine, Taurine, L–Aspartic Acid, and L–Glutamic Acid in Synaptosomal ($P_2$) Tissue: A Kinetic and Substrate Specificity Analysis" Journal of Neurochemistry, vol. 48, No. 6, 1987.
Guochuan Tsai, et al. "D–Serine Added to Antipsychotics for the Treatment of Schizophrenia" Society of Biological Psychiatry, vol. 44 pp. 1081–1089, 1998.
Michael. J. Schell, et al. "D–Serine, an endogenous synaptic modulator: Localization to astrocytes and glutamate–stimulated release" Proc. Natl. Acad. Sci. USA vol. 92, pp. 3948–3952, Apr. 1995 (Neurobiology).
Deepak Cyril D'Souza, et al. "Glycine Site Agonists of the NMDA Receptor: A Review" CNS Drug Reviews vol. 1. No. 2, pp. 227–260 1995.

Bergeron R, Meyer TM, Coyle JT, Greene RW. Modulation of N–methyl–D–aspartate receptor function by glycine transport. Proc Natl Acad Sci U S A. 1198;95:15730–4.
Danysza W, Parsons CG. Glycine and N–methyl–D–aspartate receptors: Physiological significance and possible therapeutic applications. Pharmacol. Rev. 1998;50:597–664.
Debler EA, Lajtha A (1987): High–affinity transport of gamma–aminobutyric acid, glycine, taurine, L–aspartic acid, and L–glutamatic acid in synaptosomal (P2) tissue: a kinetic and substrate specificity analysis. J. Neurochem 48:1851–6.
D'Souza DC, Charney D, Krystal J (1995): Glycine site agonists of the NMDA receptor: a review. CNS Drug Revs 1:227–260.
Hashimoto A, Oka T, Nishikawa T (1995): Extracellular concentration of endogeneous free D–serine in the rat brain as revealed by in vivo microdialysis. Neuroscience 66:635–643.
Hashimoto A, Oka T (1997): Free D–aspartate and D–serine in the mammalian brain and periphery. Prog. Neurobiol 52:325–353.
Heresco–Levy U, Javitt DC, Irmilov M, Mordel C, Horowitz A, Kelly D (1996): Double–blind, placebo–controlled, crossover trial of glycine adjuvant therapy for treatment–resistant schizophrenia. Br J Psychiatry 169:610–617.
Javitt DC, Sershen H, Hashim A, Lajtha A (1997): Reversal of phencyclidine–induced hyperactivity by glycine and the glycine uptake antagonist glycyldodecylamide. Neuropsychopharmacol 17:202–204.
Javitt DC, Frusciante MJ. (1997): Glycyldodecylamide, a phencyclidine behavioral antagonist, blocks cortical glycine uptake: Implications for schizophrenia and substance abuse. Psychopharmacol. 129: 96–98.
Javitt DC, Zylberman I, Zukin SR, Heresco–Levy U, Lindenmayer JP (1994): Amelioration of negative symptoms in schizophrenia by glycine. Am J Psychiatry 151:1234–1236.
Javitt DC, Zukin SR (1991):; Recent advances in the phencyclidine model of schizophrenia. Am J Psychiatry 148:130–8.
Javitt DC, Zukin SR (1989): Interaction of [$^3$H]MK–801 with multiple states of the N–methyl–D–aspartate receptor complex of rat brain. Proc. Nat. Acad. Sci. USA 86:740–744.
Javitt DC (1987): Negative schizophrenic symptomatology and the phencyclidine (PCP) model of schizophrenia. Hill J Psychiat 9:12–35.
Kleckner NW, Dingledine R (1988): Requirement for glycine in the activation of NMDA–receptors expressed in Xenopus ooctyes. Science 241:835–837.

(List continued on next page.)

Primary Examiner—Padmashri Ponnaluri
(74) Attorney, Agent, or Firm—Sughrue Mion, PLLC

(57) ABSTRACT

Determination of a synaptosomal D-serine transporter and use of an assay method for discovering inhibitors thereof to be used in the treatment of psychotic disorders.

8 Claims, 3 Drawing Sheets

OTHER PUBLICATIONS

Figure 1:
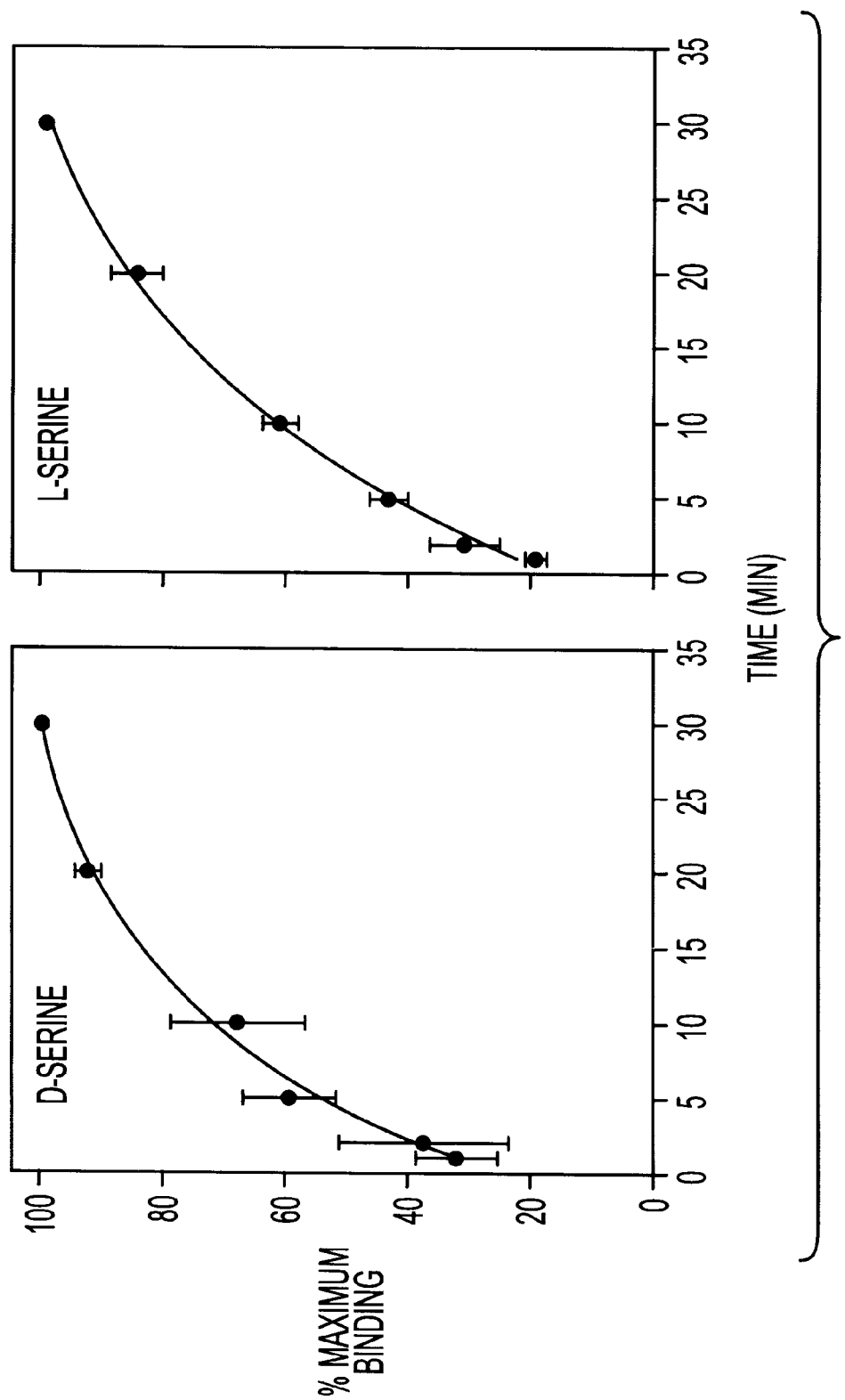

Leiderman E, Zylberman I, Javitt DC, Zukin SR, Cooper TB. Effect of high–dose oral glycine on serum levels and negative symptoms in schizophrenia. Biol. Psychiatry, in press.

Liu QR, Lopez–Corcuera B, Mandiyan S, Nelson H, Nelson N (1993): Cloning and expression of spinal cord– and brain–specific glycine transporter with novel structural features. J Biol Chem 268:22802–8.

Matsui T, Sekiguchi M, Hashimoto A, Tomita V, Nishikawa T, Wada K (1995) Functional comparison of D–serine and glycine in rodents: the effect on cloned NMDA receptors and the extracellular concentration. J Neurochem. 65:454–458.

McBain CJ, Kleckner NW, Wyrick S, Dingledine R (1989): Structural requirements for the glycine coagonist site of N–methyl–D–aspartate receptors expressed in Xenopus oocytes. Mol Pharmacol 36:556–565.

Reynold IJ, Murphy SN, Miller RJ (1987): 3H–labeled MK–801 binding to the excitatory amino acid receptor complex from rat brain is enhanced by glycine. Proc. Natl. Acad. Sci. USA 84:7744–7748.

Schell MJ, Molliver ME, Snyder SH (1995). D–serine, and endogenous synaptic modulator: localization to astrocytes and glutamate–stimulated release. Proc. Natl. Acad. Sci. USA 92:3948–3952.

Sershen H, Latha A (1995): Inhibition pattern by analogs indicates the presence of ten or more transport systems for amino acids in brain cells. J Neurochem 32:719–726.

Smith KE, Borden LA, Hartig PR, Branchek T, Weinshank RL (1992): Cloning and expression of a glycine transporter reveal colocalization with NMDA receptors, Neuron 8:927–35.

Supplisson S, Bergman C (1997): Control of NMDA receptor activation by a glycine transporter co–expressed in Xenopus oocytes. J Neurosci 17:4580–90.

Tanii Y, Nishikawa T, Hashimoto A, Takahashi K (1991): Stereoselective inhibiton by D– and L–alanine of phencyclidine–induced locomotor stimulation in the rat. Brain Res 563:281–284.

Tanii Y, Hishikawa T, Hashimoto A, Takahashi K (1994): Stereoselective antagonism by enantiomers of alanine an dserien of phencyclidine–induced hyperactivity, stereotypy and ataxia. J. Pharmacol. Exp. Ther. 269:1040–1048.

Tsai G, Yang P, Chung L–C, Lange N, Coyle JT (1998): D–serine in the treatment of schizophrenia. Biol. Psychiatry 44:1081–1089.

Wood PL (1995): The co–agonist concept: is the NMDA–associated glycine receptor saturated in vivo? Life Sci 57:301–10.

Wong EH, Knight AR, Ransom R (1987) Glycine modulated [3H]MK–801 binding to the NMDA receptor in rat brain. Eur J Pharmacol 142:487–8.

Zafra F, Aragon C, Olivares L, Danbolt NC, Gimenez C, Storm–Mathisen J (1995): Glycine transporters are differentially expressed among CNS cells. J Neurosci 15:3952–69.

Michael J. Schell, et al. "D–Serine as a Neuromoduclator: Regional and Development Localizations in Rat Brain Glia Resemble NMDA Receptors" The Journal of Neuroscience, Mar. 1, 1997, 17(5):p. 1604–1615.

\* cited by examiner

ASSAY FOR D-SERINE TRANSPORT ANTAGONIST AND USE FOR TREATING PSYCHOSIS

RELATED APPLICATIONS

This application relates to prior patent U.S. Pat. No. 5,854,286. The subject matter of the prior patent is incorporated in its entirety herein by reference thereto.

BACKGROUND

Traditional models of schizophrenia have focused on dopaminergic systems. More recent models, however, derive from the phencyclidine (PCP) model of schizophrenia (Javitt, 1987; Javitt and Zukin, 1991) and postulate that schizophrenia is associated with dysfunction or dysregulation of neurotransmission mediated at brain N-methyl-D-aspartate (NMDA)-type glutamate receptors. PCP induces psychotic symptoms in normal volunteers by blocking NMDA receptor-mediated neurotransmission. The PCP/NMDA model of schizophrenia predicts that agents which augment NMDA receptor-mediated neurotransmission should be therapeutically beneficial in schizophrenia. Treatment strategies for schizophrenia, to date, have focused on agents that potentiate NMDA receptor-mediated neurotransmission by binding to the NMDA-associated glycine binding site (=NMDA/glycine receptor). Such agents, including glycine and D-serine, reverse the behavioral effects of PCP in rodents (Toth et al., 1986; Javitt and Frusciante, 1997; Javitt et al., 1997; Tanii et al., 1994, 1991; Nilsson et al., 1997), and induce significant improvement in negative and cognitive symptoms in remitted schizophrenics (Javitt et al., 1994; Heresco-Levy et al, 1999; Tsai et al., 1998).

A limitation of the use of glycine and D-serine is the fact that large doses must be given to penetrate the blood-brain barrier. A second issue concerning the use of glycine and D-serine to augment NMDA receptor-mediated neurotransmission is that extracellular concentrations of glycine and D-serine in brain are already high (low micromolar range; Hashimoto et al., 1995; Hashomoto and Oka, 1997). Such concentrations, if they were present in the immediate vicinity of NMDA receptors, would be sufficient to saturate the NMDA/glycine site. If glycine sites were already saturated, exogenously applied glycine site agonists (e.g., glycine, D-serine) would not be effective on theoretical grounds (Woods, 1995; D'Souza, 1995). The reason that endogenous glycine does not saturate NMDA receptors under physiological conditions is that such receptors are protected from general extracellular levels through the action of glycine transporters (glycine uptake pumps) that are co-localized with NMDA receptors (Smith et al., 1992; Liu et al., 1993; Javitt and Frusciante, 1997; Javitt et al., 1997; Supplison and Bergman, 1998; Bergeron et al, 1998; Berger et al, 1998; Danysza and Parsons, 1998). These transporters maintain low glycine levels in the immediate vicinity of NMDA receptors. The transporters, however, can be saturated by sufficient doses of glycine, permitting elevated levels to potentiate NMDA neurotransmission. Elevations of glycine levels in the immediate vicinity of NMDA receptors can also be induced by blocking glycine uptake. U.S. Pat. No. 5,837,730 to the current inventor provided the first evidence that an identified glycine transport inhibitor, glycyldodecylamide (GDA), was able to exert glycine-like, anti-PCP behavioral effects in rodents, and thus the first evidence that glycine transport inhibitors should exert glycine-like amelioration of negative and cognitive symptoms in schizophrenia.

SUMMARY OF THE INVENTION

The present invention relates to the use of D-serine uptake antagonists in the treatment of schizophrenia. D-Serine, like glycine, has been shown to be effective in treatment of persistent negative symptoms of schizophrenia (Tsai et al., 1998). However, as with glycine, sufficient concentrations of D-serine are already present in brain that NMDA/glycine sites (the molecular target of D-serine) would be saturated under normal circumstances. This appears to be true both in cortex and subcortical structures, where micromolar concentrations have been documented (Hashimoto et al., 1995, Hashimoto and Oka, 1997; Matsui et al., 1995). If the NMDA/glycine site were saturated by endogenous D-serine, then neither exogenous glycine or exogenous D-serine would have significant neurochemical or behavioral effects since both these agents share a common target (i.e., the NMDA/glycine site). The fact that glycine and serine do potentiate NMDA receptor-mediated neurotransmission suggests that for D-serine, as with glycine, there must be an endogenous process that "protects" NMDA receptors from extracellular D-serine. Although no specific D-serine transport system has yet been described in brain, existence of such a system would explain the fact that NMDA/glycine sites are not saturated by D-serine in vivo. If such a system were identified, blockade of such a system would be expected to yield behavioral and neurochemical effects analogous to those produced by (1) large doses of D-serine, (2) large doses of glycine, or (3) glycine transport inhibitors. The similar effects of D-serine, glycine and glycine transport inhibitors include (1) potentiation of NMDA receptor-mediated neurotransmission and (2) reversal of PCP-induced behavioral and neurochemical effects. Agents that potentiate NMDA receptor-mediated neurotransmission in vivo have shown effectiveness in the treatment of persistent negative and cognitive symptoms of schizophrenia.

The present application provides the first description of a synaptosomal D-serine transport system capable of maintaining submicromolar concentrations of D-serine. Based upon that demonstration, the present application claims use of D-serine transport inhibitors, at doses sufficient to augment brain D-serine levels, for the treatment of schizophrenia. Although n mnific compounds are claimed, the application describes an assay system for identifying useful D-serine transport inhibitors. ods for synthesis and screening of such compounds based upon this assay are readily apparent to practioners skilled in the art.

Sections below detail current (1) state-of-the-art regarding existence of D-serine transport systems in brain and (2) description of a novel, high affinity D-serine transport system identified in synaptosomal preparations.

THE DRAWING

Figure 2:
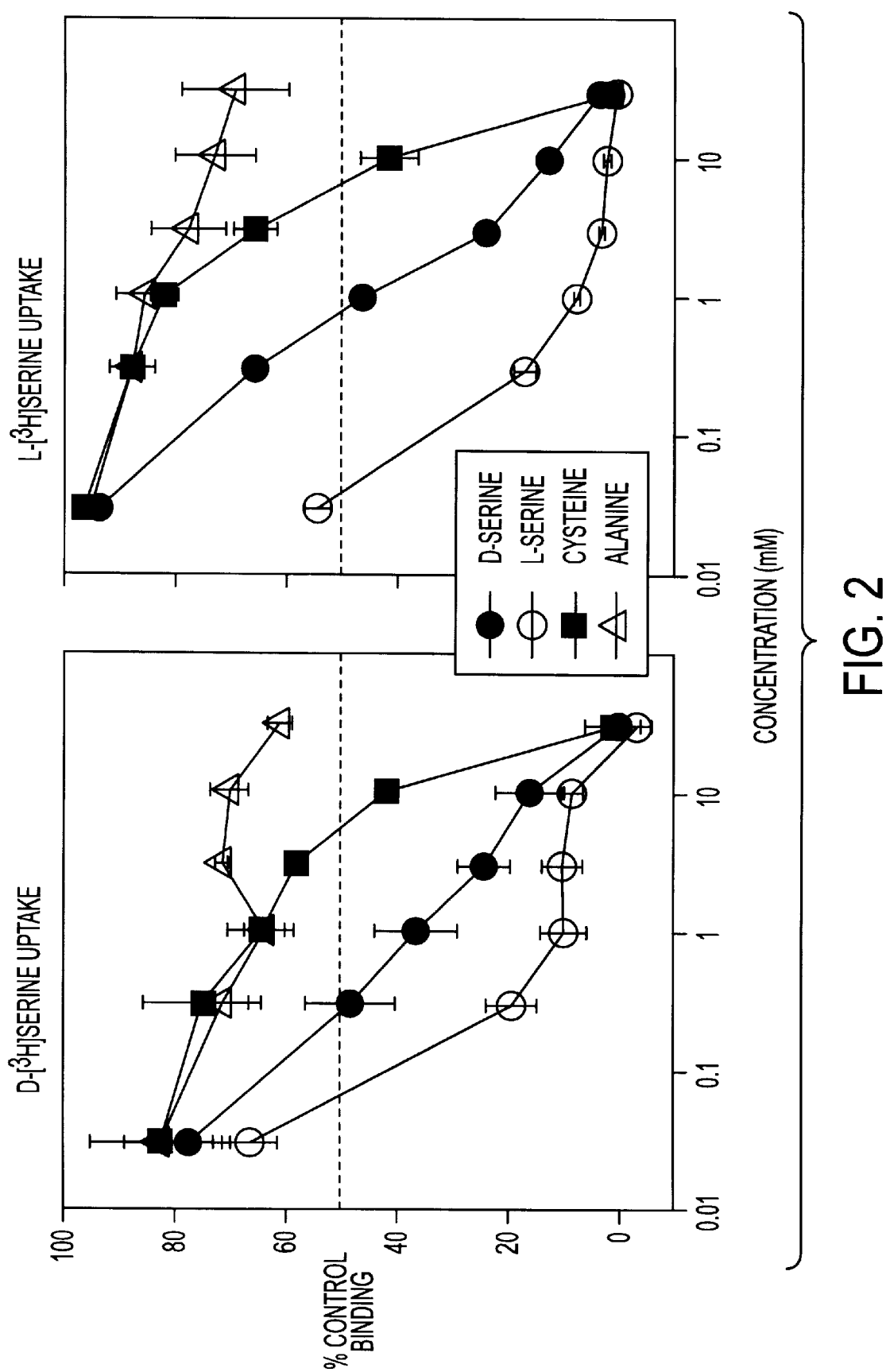
Figure 3:
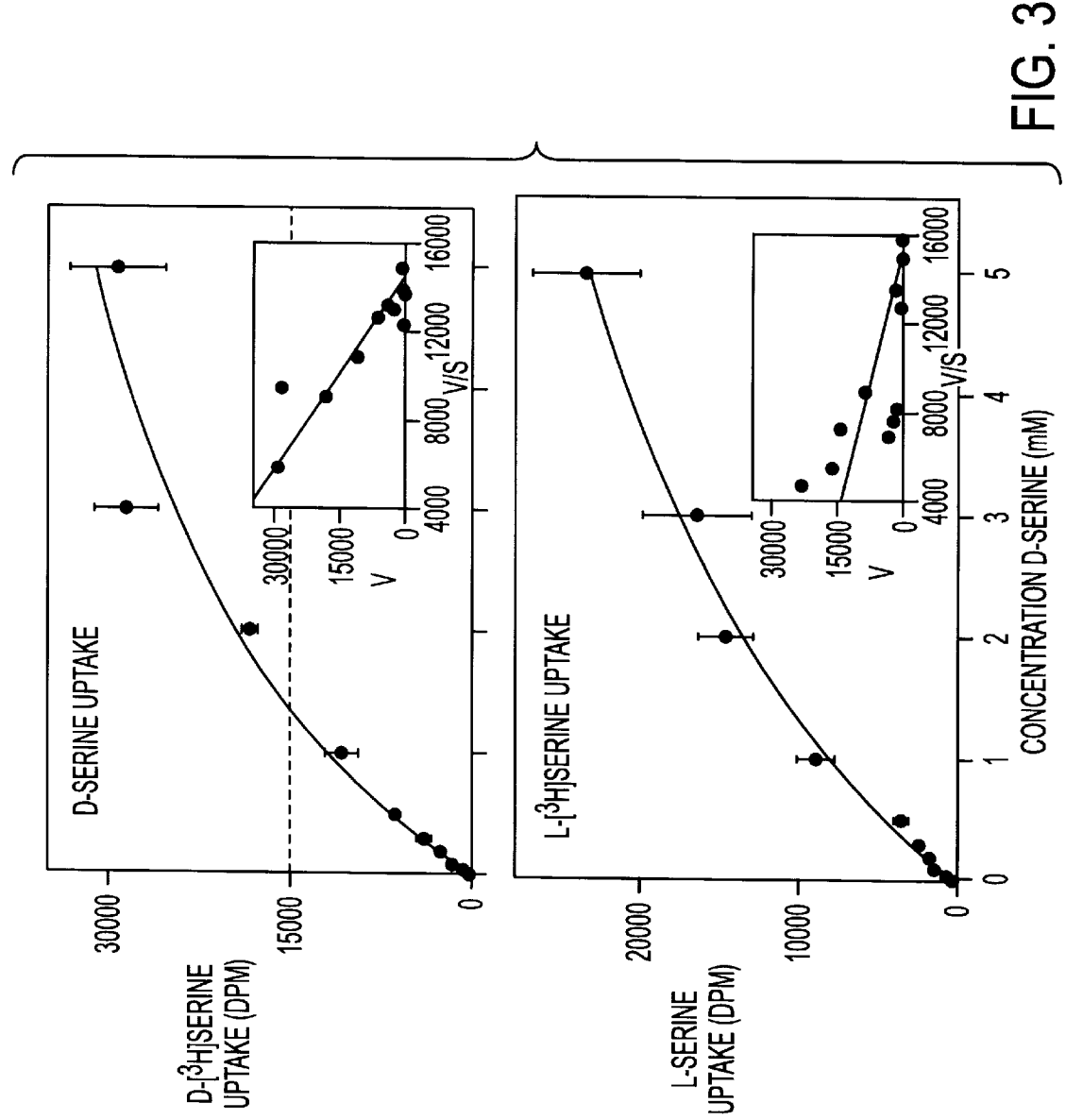

FIGS. 1–3 plot the results obtained in the Experimental Section of the Detailed Description of the Invention, hereinafter.

DETAILED DESCRIPTION OF THE INVENTION

Current state-of-the-art Brain is known to contain multiple amino acid transport systems, including system "Gly", which is specialized for uptake of glycine, system which is specialized for uptake of Alanine, system which which is specialized for uptake of Leucine, and system "ASC" which is specialized for uptake of Alanine, Serine and Cysteine (Sershen and Lajtha, 1979; Hashimoto and Oka, 1997).

Serine transport, including transport of both L- and D-isomers of serine, is generally considered to occur via system ASC (Hashimoto and Oka, 1997), although transport may also occur though system L (Sershen and Lajtha, 1979). The hallmark of this system is high affinity for alanine. Two ASC-like transporters have recently been cloned and have been termed ASCT1 (Arriza et al., 1993) and ASCT2 (Utsunomiya-Tate et al., 1996). Studies with cloned transporters have confirmed that ASC-family transporters show highest affinity for L-alanine, along with high affinity for L-cysteine and L-serine, and stereoselectivity for L- vs. D-amino acids. A related transporter, termed SATT was found to have differential affinity for serine and cysteine. However, this transporter was found not to be sensitive to D-serine (Shafqat et al., 1993). Based on the relatively low affinity of these transporters for D-amino acids, Hashimoto et al. (1997) concluded that "further study is needed to clarify a specific transport system for D-serine in mammals."

D-Serine transport has also been studied in glioma cells (Hayashi et al., 1997) and astocyte cultures (Schell et al., 1995). Glia have also been shown to accumulate exogenously administered D-serine in vivo (Wako et al., 1995; Schell et al., 1995). Transport in these cells, like transport through cloned receptors, was found to be inhibited most strongly by L-cysteine, L-alanine, and L-serine. D-Serine was transported, but affinity for D-serine was approximately 20-fold lower than affinity for L-serine. This finding is consistent with glial D-serine uptake being mediated by system ASC transporters. The relative insensitivity of these transporters to D-serine makes it unlikely that they regulate synaptic D-serine levels in vivo.

Further suggestion that additional D-serine transporters are present in brain comes from a study by Tanii et al. (1994). In that study, they observed that intracerebroventricularly administered D-alanine was significantly more potent in reversing PCP-induced hyperactivity than was intracerebroventricularly administered D-serine, even though D-serine is more potent in binding to the NMDA/ glycine site. This finding suggests the existence of a brain transporter with higher affinity for serine and alanine. Such a pattern would be opposite to the known selectivity pattern of system ASC. In discussing relative potency of D-serine to other amino acids, Tanii et al. (1994) postulated the existence of "specific metabolizing systems" for D-serine, but did not specifically postulate the existence of a selective transporter. Moreover, despite the recognition that D-serine serves as an endogenous agonist of NMDA receptors, use of selective D-serine transport antagonists in the treatment of schizophrenia has not been previously suggested.

Demonstration of a novel D-serine Transporter in Synaptosomes

Based upon the observation that glycine is effective in the treatment of schizophrenia (Javitt and Zukin, U.S. Pat. No. 5,854,286), it can be concluded that glycine sites are not saturated under normal physiological conditions in schizophrenia. Extracellular concentrations of D-serine in brain are known to be above those necessary to saturate NMDA/ glycine sites. These findings raise the possibility that brain may contain a D-serine transporter that protects NMDA receptors from extracellular D-serine concentrations. Actions of such a transporter would be analogous to the role played by glycine transporters in protecting NMDA receptors from extracellular glycine levels. Use of glycine transport inhibitors in treatment of schizophrenia were described in a separate application (Javitt, U.S. Pat. No. 5,837,730). The present application demonstrates the existence of a novel D-serine transporter, supporting the feasibility of use of D-serine transport inhibitors in treatment of schizophrenia.

Experimental Section

In order to investigate the existence of a synaptosomal D-serine transporter, synaptosomal (P2) preparations were prepared from rodent brain. This preparation permits identification of transport mechanisms on pre- and post-synaptic terminals and so is crucial for identifying systems that may be co-localized with NMDA receptors which are located on synaptic terminals.

In contrast, the majority of transport studies are performed using either cloned transporters or brain slices, which provide less specificity for identifying perisynaptic transport mechanisms. Membranes were suspended in oxygenated artificial CSF and incubated in the presence of L- or D-[$^3$H] serine, as appropriate. Incubation was terminated by filtration under reduced pressure through Whatman GF/B filters.

For initial studies, uptake was measured over a 30 min. period (FIG. 1). Uptake of L- and D-[$^3$H]serine was linear over the first 10 min. with a tendency for plateau by 30 min. Uptake was unaffected by incubation with the selective system L antagonist BCH (2-aminobicyclo (2,2,1)heptane-2 carboxylic acid, 10 mM). Effects of the system ASC substrates alanine, cysteine and serine were evaluated at concentrations between 0.03 and 30 mM (FIG. 2). Complete inhibition of serine uptake was obtained with either L- or D-serine. In both cases, L-serine showed greater potency that D-serine in inducing inhibtion. Inhibition was also obtained with cysteine, although potency of cysteine was significantly less than that of either L- or D-serine. In contrast, only partial inhibition was observed with alanine, even at doses as high as 30 mM. This pattern of inhibition is opposite to that of system ASC, indicating that the observed L-and D-serine uptake is mediated primarily by a system other than system ASC. This system has not been previously described.

Finally, in order to characterize kinetics of uptake, saturation studies were conducted following 5 min. incubation with concentrations of L- and D-serine between 0.01 and 5 mM (FIG. 3). Studies were conducted in the presence of 30 mM L-alanine to prevent uptake through system ASC. Even in the presence of alanine, significant uptake of L- and D-serine was observed. Saturation of D-serine binding was observed between 3 and 5 mM, with half-maximal binding occurring between 1–2 mM. A Michaelis-Menton constant (Km) of 3.33 mM was obtained by non-linear regression. An Eadie-Hofstee plot demonstrated linear uptake, supporting the concept that this uptake occurs via a discrete, alanine-insenstive D-serine transport system with approximately equal affinity for D- and L-serine. The presence of such a system in synaptosomal tissue from rodent forebrain indicates that it may play a crucial role in regulation of D-serine concentrations in the vicinity of NMDA receptors. Inhibition of this system would be expected to increase local D-serine concentrations in brain, leading to augmentation of NMDA receptor-mediated neurotransmission. Inhibition of selective serine uptake would thus constitute a novel mechanism for stimulation of NMDA receptor-mediated neurotransmission in vivo.

In summary, a prior patent U.S. Pat. No. 5,854,286 described efficacy of glycine and other NMDA agonist in the treatment of schizophrenia. A prior patent U.S. Pat. No. 5,837,730, described use of glycine transport inhibitors as potentiators of NMDA receptor-mediated neurotransmission and potential treatments for persistent symptoms of schizophrenia. The present study discloses use of D-serine-transport inhibitors for a similar purpose. An assay system for identifying D-serine-transport inhibitors is described.

Variations of the invention will be apparent to the skilled artisan.

REFERENCES

Bergeron R, Meyer T M, Coyle J T, Greene R W. Modulation of N-methyl-D-aspartate receptor function by glycine transport. Proc Natl Acad Sci U S A. 1998;95:15730–4.

Danysza W, Parsons C G. Glycine and N-methyl-D-aspartate receptors: Physiological significance and possible therapeutic applications. Pharmacol. Rev. 1998;50:597–664.

Debler E A, Lajtha A (1987): High-affinity transport of gamma-aminobutyric acid, glycine, taurine, L-aspartic acid, and L-glutamatic acid in synaptosomal (P2) tissue: a kinetic and substrate specificity analysis. J Neurochem 48:1851–6.

D—Souza D C, Charney D, Krystal J (1995): Glycine site agonists of the NMDA receptor: a review. CNS Drug Revs 1:227–260.

Hashimoto A, Oka T, Nishikawa T (1995): Extracellular concentration of endogenous free D-serine in the rat brain as revealed by in vivo microdialysis. Neuroscience 66:635–643.

Hashimoto A, Oka T (1997): Free D-aspartate and D-serine in the mammalian brain and periphery. Prog. Neurobiol 52:325–353.

Heresco-Levy U, Javitt D C, Irmilov M, Mordel C, Horowitz A, Kelly D (1996): Double-blind, placebo-controlled, crossover trial of glycine adjuvant therapy for treatment-resistant schizophrenia. Br J Psychiatry 169:610–617.

Javitt D C, Sershen H, Hashim A, Lajtha A (1997): Reversal of phencyclidine-induced hyperactivity by glycine and the glycine uptake antagonist glycyldodecylamide. Neuropsychopharmacol 17:202–204.

Javitt D C, Frusciante M J. (1997): Glycyldodecylamide, a phencyclidine behavioral antagonist, blocks cortical glycine uptake: Inplications for schizophrenia and substance abuse. Psychopharnacol. 129: 96–98.

Javift D C, Zylberman I, Zukin S R, Heresco-Levy U, Lindenmayer JP (1994): Amelioration of negative symptoms in schizophrenia by glycine. Am J Psychiatry 151:1234–1236.

Javitt D C, Zukin S R (1991): Recent advances in the phencyclidine model of schizophrenia. Am J Psychiatry 148:1301–8.

Javitt D C, Zukin S R (1989): Interaction of [$^3$H]MK-801 with multiple states of the N-methyl-D-aspartate receptor complex of rat brain. Proc. Nat. Acad. Sci. USA 86:740–744.

Javitt D C (1987): Negative schizophrenic symptomatology and the phencyclidine (PCP) model of schizophrenia. Hill J Psychiat 9:12–35.

Kleckner N W, Dingledine R (1988): Requirement for glycine in the activation of NMDA-receptors expressed in Xenopus ooctyes. Science 241:835–837.

Leiderman E, Zylberman I, Javitt D C, Zukin S R, Cooper T B. Effect of high-dose oral glycine on serum levels and negative symptoms in schizophrenia. Biol. Psychiatry, 1996;39:213–215.

Liu Q R, Lopez-Corcuera B, Mandiyan S, Nelson H, Nelson N (1993): Cloning and expression of spinal cord- and brain-specific glycine transporter with novel structural features. J Biol Chem 268:22802–8.

Matsui T, Sekiguchi M, Hashimoto A, Tomita V, Nishikawa T, Wada K (1995) Functional comparison of D-serine and glycine in rodents: the effect on cloned NMDA receptors and the extracellular concentration. J Neurochem. 65:454–458.

McBain C J, Kleckner N W, Wyrick S, Dingledine R (1989): Structural requirements for the glycine coagonist site of N-methyl-D-aspartate receptors expressed in Xenopus oocytes. Mol Pharmacol 36:556–565.

Reynold I J, Murphy SN, Miller R J (1987): 3H-labeled MK-801 binding to the excitatory amino acid receptor complex from rat brain is enhanced by glycine. Proc. Natl. Acad. Sci. USA 84:7744–7748.

Schell M J, Molliver M E, Snyder S H (1995). D-serine, an endogenous synaptic modulator: localization to astrocytes and glutamate-stimulated release. Proc. Natl. Acad. Sci. USA 92:3948–3952.

Sershen H, Latha A (1995): Inhibition pattern by analogs indicates the presence of ten or more transport systems for amino acids in brain cells. J Neurochem 32:719–726.

Smith K E, Borden L A, Hartig P R, Branchek T, Weinshank R L (1992): Cloning and expression of a glycine transporter reveal colocalization with NMDA receptors. Neuron 8:927–35.

Supplisson S, Bergman C (1997): Control of NMDA receptor activation by a glycine transporter co-expressed in Xenopus oocytes. J Neurosci 17:4580–90.

Tanii Y, Nishikawa T, Hashimoto A, Takahashi K (1991): Stereoselective inhibition by D- and L-alanine of phencyclidine-induced locomotor stimulation in the rat. Brain Res 563:281–284.

Tanii Y, Hishikawa T, Hashimoto A, Takahashi K (1994): Stereoselective antagonism by enantiomers of alanine an dserien of phencyclidine-induced hyperactivity, stereotypy and ataxia. J. Pharmacol. Exp. Ther. 269:1040–1048.

Tsai G, Yang P, Chung L-C, Lange N, Coyle J T (1998): D-serine in the treatment of schizophrenia. Biol. Psychiatry 44:1081–1089.

Wood P L (1995): The co-agonist concept: is the NMDA-associated glycine receptor saturated in vivo? Life Sci 57:301–10.

Wong E H, Knight A R, Ransom R (1987) Glycine modulates [3H]MK-801 binding to the NMDA receptor in rat brain. Eur J Pharmacol 142:487–8.

Zafra F, Aragon C, Olivares L, Danbolt N C, Gimenez C, Storm-Mathisen J (1995): Glycine transporters are differentially expressed among CNS cells. J Neurosci 15:3952–69.

What is claimed:

1. An assay method for identifying antagonists of non-system ASC-mediated D-serine-transport comprising incubating synaptically derived brain membrane fragments ("synaptosomes") with labelled D- or L-serine and with a chemical to be tested as a D-Serine transport antagonist and thereafter measuring the D- or L-Serine uptake in comparison with a control "wherein a decrease in labeled D- or L-serine uptake in the presence of the chemical to be tested in comparison with the control identifies the chemical as a potential non-system ASC transport antagonist".

2. The assay method of claim 1 wherein the D- or L-Serine is radioactively labelled.

3. The assay method of claim 1 wherein the incubation is conducted in the presence of a selective inhibitor of system ASC.

4. The assay method of claim 1 wherein the D-or-L-serine are labeled with radioactive label.

5. The assay method of claim 3 wherein the selective inhibitor is alanine.

6. An assay method for identifying antagonists of non-system ASC-mediated D-serine-transport comprising incubating synaptically derived brain membrane fragments ("synaptosomes") with a labeled substrate for the non-system ASC transport system and with a chemical to be tested as a D-serine transport antagonist and thereafter measuring the substrate uptake in comparison with a control "wherein a decrease in substrate uptake in the presence of the chemical to be tested in comparison with the control identifies the chemical as a potential non-system ASC transport antagonist".

7. The assay method of claim 6 wherein the incubation is conducted in the presence of a selective inhibitor of system ASC.

8. The assay method of claim 7 wherein the selective inhibitor is alanine.

* * * * *